United States Patent
Zhu et al.

(10) Patent No.: US 11,043,988 B2
(45) Date of Patent: Jun. 22, 2021

(54) SYSTEMS FOR PROVIDING WIRELESS POWER TO DEEP IMPLANTED DEVICES

(71) Applicant: Verily Life Sciences LLC, Mountain View, CA (US)

(72) Inventors: Jiang Zhu, Cupertino, CA (US); Stephen O'Driscoll, San Francisco, CA (US)

(73) Assignee: VERILY LIFE SCIENCES LLP, South San Francisco, CA (US)

( * ) Notice: Subject to any disclaimer, the term of this patent is extended or adjusted under 35 U.S.C. 154(b) by 247 days.

(21) Appl. No.: 15/071,113

(22) Filed: Mar. 15, 2016

(65) Prior Publication Data

US 2017/0272123 A1    Sep. 21, 2017

(51) Int. Cl.
*H02J 50/10* (2016.01)
*H04B 5/00* (2006.01)
(Continued)

(52) U.S. Cl.
CPC ......... *H04B 5/0037* (2013.01); *A61N 1/3787* (2013.01); *A61N 1/37229* (2013.01);
(Continued)

(58) Field of Classification Search
CPC .. A61N 1/37229; A61N 1/3787; H01Q 1/273; H01Q 7/00; H01Q 19/00;
(Continued)

(56) References Cited

U.S. PATENT DOCUMENTS

| 6,099,482 | A | * | 8/2000 | Brune | A01K 11/007 |
| | | | | | 600/549 |
| 8,373,252 | B1 | | 2/2013 | DeBaets | |

(Continued)

FOREIGN PATENT DOCUMENTS

| CN | 101005800 | 7/2007 |
| CN | 102112045 | 6/2011 |

(Continued)

OTHER PUBLICATIONS

Michael Mark, "Powering mm-Size Wireless Implants for Brain-Machine Interfaces," Electrical Engineering and Computer Sciences University of California at Berkley, Technical Report No. UCB/EECS-2011-130, http://www.eecs.berkeley.edu/Pubs/TechRots/2011/EECS-2011-130.html, Dec. 12, 2011 (152 pages).

(Continued)

*Primary Examiner* — Daniel Kessie
*Assistant Examiner* — Brian K Baxter
(74) *Attorney, Agent, or Firm* — Kilpatrick Townsend & Stockton LLP (57) ABSTRACT

The present disclosure relates to systems for providing wireless power to implanted devices. Consistent with some embodiments, an antenna system for providing wireless power to an implanted device includes a primary antenna loop and at least one parasitic antenna loop. The primary antenna loop is configured to receive power from a power source and radiate the power toward the implanted device. The at least one parasitic antenna loop is configured to absorb a portion of the radiated power and to reradiate the absorbed power toward the implanted device. The power radiated by the primary antenna loop and the power reradiated by the at least one parasitic antenna loop form a wireless power transmission pattern broadly distributed at the surface of the individual's skin and becomes more focused as it travels into the individual's body toward the implanted device. The broad distribution pattern at the surface of the skin reduces the specific absorption rate of the transmission while focusing the transmission as it toward the implanted device improves the antenna system's transfer efficiency.

21 Claims, 8 Drawing Sheets

(51) Int. Cl.

| | |
|---|---|
| *A61N 1/378* | (2006.01) |
| *H01Q 7/00* | (2006.01) |
| *A61N 1/372* | (2006.01) |
| *H01Q 1/27* | (2006.01) |
| *H01Q 19/00* | (2006.01) |
| *A61B 5/00* | (2006.01) |
| *H01Q 3/26* | (2006.01) |
| *H01Q 3/44* | (2006.01) |
| *H02J 50/50* | (2016.01) |

(52) U.S. Cl.
CPC .............. *H01Q 1/273* (2013.01); *H01Q 7/00* (2013.01); *A61B 5/0031* (2013.01); *A61B 5/4064* (2013.01); *A61B 2560/0219* (2013.01); *H01Q 3/2635* (2013.01); *H01Q 3/446* (2013.01); *H01Q 19/00* (2013.01); *H02J 50/10* (2016.02); *H02J 50/50* (2016.02); *H04B 5/0075* (2013.01)

(58) Field of Classification Search
CPC ....... H01Q 3/2635; H01Q 3/446; H02J 50/10; H02J 50/23; H02J 5/005; H02J 7/025; H02J 17/00; H04B 5/0037; H04B 5/0075; B60L 11/182; A61B 2560/0219; A61B 5/0031; A61B 5/4064; H01F 38/14
USPC .......................................................... 307/104
See application file for complete search history.

(56) References Cited

U.S. PATENT DOCUMENTS

| | | | |
|---|---|---|---|
| 8,634,928 B1 | 1/2014 | O'Driscoll et al. | |
| 9,672,393 B1 | 6/2017 | Zhu et al. | |
| 9,884,180 B1 | 2/2018 | Ho et al. | |
| 10,075,008 B1 | 9/2018 | Bell et al. | |
| 10,099,049 B2 | 10/2018 | Ho et al. | |
| 10,230,266 B1* | 3/2019 | Leabman | H02J 7/0042 |
| 10,263,432 B1* | 4/2019 | Leabman | H02J 50/20 |
| 10,291,055 B1* | 5/2019 | Bell | H02J 7/025 |
| 10,291,066 B1* | 5/2019 | Leabman | H02J 7/025 |
| 2005/0228268 A1* | 10/2005 | Cole | A61B 5/1112 600/420 |
| 2007/0149162 A1 | 6/2007 | Greene et al. | |
| 2008/0103558 A1 | 5/2008 | Wenzel et al. | |
| 2009/0134712 A1 | 5/2009 | Cook et al. | |
| 2010/0033021 A1 | 2/2010 | Bennett | |
| 2010/0114253 A1 | 5/2010 | Wahlstrand et al. | |
| 2011/0281535 A1 | 11/2011 | Low et al. | |
| 2012/0228563 A1 | 9/2012 | Fuller et al. | |
| 2013/0194540 A1 | 8/2013 | Pugh et al. | |
| 2013/0200721 A1 | 8/2013 | Kurs et al. | |
| 2013/0307753 A1 | 11/2013 | Andrenko | |
| 2014/0028111 A1 | 1/2014 | Hansen et al. | |
| 2014/0125275 A1 | 5/2014 | Low et al. | |
| 2014/0292587 A1 | 10/2014 | Yarga et al. | |
| 2014/0313099 A1 | 10/2014 | Pajona et al. | |
| 2015/0295314 A1 | 10/2015 | Oh | |
| 2015/0333413 A1 | 11/2015 | Piazza et al. | |
| 2015/0333529 A1* | 11/2015 | Leabman | H02J 50/40 307/104 |
| 2016/0104941 A1 | 4/2016 | Lee et al. | |
| 2016/0126744 A1* | 5/2016 | Jeong | H02J 17/00 307/104 |
| 2016/0220828 A1 | 8/2016 | Yan Poon et al. | |
| 2016/0344238 A1 | 11/2016 | Yeh et al. | |
| 2016/0352000 A1 | 12/2016 | Ohno et al. | |
| 2017/0230084 A1 | 8/2017 | Zhu et al. | |
| 2017/0331330 A1 | 11/2017 | Yeo et al. | |
| 2018/0076670 A1 | 3/2018 | O'Driscoll et al. | |
| 2019/0150884 A1 | 5/2019 | Maharbiz et al. | |
| 2020/0101296 A1 | 4/2020 | Forsell | |

FOREIGN PATENT DOCUMENTS

| | | |
|---|---|---|
| CN | 104736053 | 6/2015 |
| CN | 104767284 | 7/2015 |
| CN | 104941017 | 9/2015 |
| JP | 2011514221 | 5/2011 |
| JP | 2015112169 | 6/2015 |
| WO | 2009115102 | 9/2009 |
| WO | 2010042054 | 4/2010 |
| WO | 2011046674 | 4/2011 |
| WO | 2015039108 | 3/2015 |
| WO | 2015179225 | 11/2015 |

OTHER PUBLICATIONS

Jayant Charthad et al., "A mm-Sized Implantable Medical Device (IMD) With Ultrasonic Power Transfer and a Hybrid Bi-Directional Data Link," IEEE Journal of Solid-State Circuits, vol. 50, No. 8, Aug. 2015 (13 pages).
Jung-Ick Moon et al., "Novel Energy Harvesting Antenna Design Using a Parasitic Radiator," Progress in Electromagnetics Research, vol. 142, 545-557, 2013 (13 pages).
John S. Ho et al., "Wireless Power Transfer to Deep-Tissue Microimplants," Proc Natl Acad Sci USA, Jun. 3, 2014; 111(22):7974-7979 (12 pages).
International Patent Application No. PCT/US2017/021403, International Search Report and WRitten Opinion dated May 23, 2017.
U.S. Appl. No. 15/696,838 , "Non-Final Office Action", dated Jun. 28, 2019, 15 pages.
European Application No. EP17712625.7 , "Office Action", dated Oct. 8, 2019, 6 pages.
International Application No. PCT/US2017/050551 , "International Preliminary Report on Patentability", Mar. 21, 2019, 11 pages.
International Application No. PCT/US2017/050551 , "International Search Report and Written Opinion", Nov. 24, 2017, 16 pages.
U.S. Appl. No. 15/696,838 , "Final Office Action", dated Jan. 7, 2020, 19 pages.
U.S. Appl. No. 15/696,838, Final Office Action, dated Sep. 15, 2020, 12 pages.
European Application No. 16829381.9, Office Action, dated Oct. 13, 2020, 4 pages.
U.S. Appl. No. 15/696,838 , Non-Final Office Action, dated May 29, 2020, 14 pages.
Chinese Application No. CN201680083783.1 , Notice of Decision to Grant, dated Jul. 6, 2020, 5 pages.
Chinese Application No. CN201680083783.1 , Office Action, dated Sep. 29, 2019, 11 pages.
Chinese Application No. CN201680083783.1 , Office Action, dated Apr. 10, 2019, 12 pages.
Chinese Application No. CN201680083783.1 , Office Action, dated Apr. 1, 2020, 8 pages.
European Application No. EP16829381.9 , Office Action, dated Jun. 4, 2019, 5 pages.
European Application No. EP16829381.9 , Office Action, dated Nov. 13, 2019, 6 pages.
Japanese Application No. JP2018-559669 , Notice of Decision to Grant, dated Jul. 9, 2020, 3 pages.
International Application No. PCT/US2016/069426 , International Preliminary Report on Patentability, dated Aug. 16, 2018, 9 pages.
International Application No. PCT/U52016/069426 , International Search Report and Written Opinion, dated Apr. 20, 2017, 11 pages.
European Application No. 17712625.7, Notice of Decision to Grant, dated Nov. 26, 2020, 2 pages.
Japanese Application No. 2018-541624, Office Action, dated Mar. 12, 2021, pages

* cited by examiner

SYSTEMS FOR PROVIDING WIRELESS POWER TO DEEP IMPLANTED DEVICES

BACKGROUND

The present disclosure generally relates to wireless power generation systems. More specifically, and without limitation, the present disclosure relates to non-invasive systems for providing wireless power to an implanted device in an individual or other living being.

Implanted devices, such as devices implanted in the body of an individual or other living being, may be used for various functions. For example, an endoscopic capsule may be implanted to perform telemetry within the gastrointestinal tract of a patient. As another example, a brain-computer interface may be implanted to augment and/or repair various cognitive and sensory-motor functions. Yet another example is a micro sensor for sensing physiological parameters of an individual. These and other implanted devices may include various subsystems for collecting data, providing outputs based on collected data, performing calculations, and/or carrying out various instructions.

Various techniques and systems exist for powering an implanted device. One technique includes providing power to an implanted device through wireless power transfer using an ex-vivo antenna. This approach has a number of challenges and shortcomings. One challenge is that the implanted device may reside deep within the body (e.g., greater than 10 mm below the surface of the skin), and therefore wireless power signals must travel through multiple layers of body tissue (including layers of skin, fat, and muscle) before reaching the implanted device. As a result, wireless power signals become increasingly attenuated as they travel through successive layers of body tissue, resulting in poor power transfer efficiency.

One solution to the transfer efficiency challenge is to simply increase transmit power of the ex-vivo antenna. While this may be a viable solution in certain scenarios, it may not be desirable in the context of the human body. Indeed, various government and health regulations may limit the amount of energy that can be radiated into the human body. Accordingly, existing systems and methods for providing wireless power do not address the challenge of efficiently delivering power to implanted devices, while minimizing the amount of power radiated into the human body.

SUMMARY

The present disclosure includes systems for wirelessly providing power to implanted devices. In illustrative embodiments, an ex-vivo antenna system is capable of transmitting a focused wireless power transmission to an implanted device.

In accordance with one example embodiment, an ex-vivo antenna system is provided for wirelessly powering an implanted device. As disclosed herein, the antenna system may include a primary antenna loop and at least one parasitic antenna loop. The primary antenna loop receives power from a power source and radiates the power toward the implanted device. The at least one parasitic antenna loop absorbs a portion of the radiated power and reradiates the absorbed power toward the implanted device. The power radiated by the primary antenna loop and the power reradiated by the at least one parasitic antenna loop form a wireless power transmission pattern broadly distributed at the surface of the individual's skin and becomes more focused as it travels into the individual's body toward the implanted device.

In accordance with another example embodiment, an ex-vivo antenna system is provided for wirelessly powering an implanted device. In this embodiment, the antenna system may include a primary antenna loop for receiving power from a power source and radiating the power toward an implanted device, and a plurality of parasitic antenna loops for forming a constructive interference pattern that focuses the radiated power as it travels toward the implanted device.

In accordance with yet another example embodiment, an ex-vivo antenna system for wirelessly powering an implanted device is disclosed. As disclosed herein, the antenna system may include a primary antenna loop for receiving power from a power source and radiating the power toward an implanted device, a matching network for connecting the primary antenna loop to the power source, and a plurality of parasitic antenna loops for reducing the specific absorption rate of the radiated power at the surface of the skin of the individual and for improving the transfer efficiency of the radiated power by focusing the radiated power as it travels toward the implanted device. The primary antenna loop and matching network are printed on a first surface of a substrate, while the parasitic antenna loops are printed on a second surface of the substrate.

Before explaining example embodiments of the present disclosure in detail, it is to be understood that the disclosure is not limited in its application to the details of construction and to the arrangements of the components set forth in the following description or illustrated in the drawings. The disclosure is capable of embodiments in addition to those described and of being practiced and carried out in various ways. Also, it is to be understood that the phraseology and terminology employed herein, as well as in the abstract, are for the purpose of description and should not be regarded as limiting.

As such, those skilled in the art will appreciate that the conception and features upon which this disclosure is based may readily be utilized as a basis for designing other structures, methods, and systems for carrying out the several purposes of the present disclosure. Furthermore, the claims should be regarded as including such equivalent constructions insofar as they do not depart from the spirit and scope of the present disclosure.

BRIEF DESCRIPTION OF DRAWINGS

The accompanying drawings, which are incorporated in and constitute part of this specification, and together with the description, illustrate and serve to explain the principles of various exemplary embodiments.

DETAILED DESCRIPTION OF EXAMPLE EMBODIMENTS

Embodiments of the present disclosure provide improved systems for providing power to implanted devices. The disclosed systems are capable of maximizing the amount of power received at an implanted device, while minimizing the amount of power absorbed by the body in which the device is implanted. The disclosed systems are capable of being used to provide power to devices implanted at various depths, including depths of 10-150 mm below the surface of the skin.

In accordance with some embodiments, the disclosed systems may include an ex-vivo antenna system capable of radiating power wirelessly to an implanted device. As radiated power travels further into the body, it becomes more and more attenuated. In order to combat this attenuation, and to maximize the amount of power received at the implanted device, while minimizing the amount of power by the body, the disclosed antenna system is capable of focusing the radiated power as it travels further into the body. The focusing may be achieved through a combination of, for example, a primary antenna loop and one or more parasitic antenna loops. The primary antenna loop may receive power generated by a power source and may radiate the generated power. The parasitic loops (also referred to as passive radiators) absorb some of the radiated power and redirect the absorbed power toward the implanted device. The combination of primary loop and parasitic loops are therefore capable of forming an efficient wireless power transmission pattern that is broadly distributed at the surface of the skin while becoming more and more focused as it travels into the body toward the implanted device. Accordingly, the power absorbed by the body resulting from poor antenna directivity (measured as the specific absorption rate) can be minimized while improving power transfer efficiency through the use of constructive interference patterns.

Reference will now be made in detail to the embodiments implemented according to the disclosure, the examples of which are illustrated in the accompanying drawings. Wherever possible, the same reference numbers will be used throughout the drawings to refer to the same or like parts.

Figure 1:
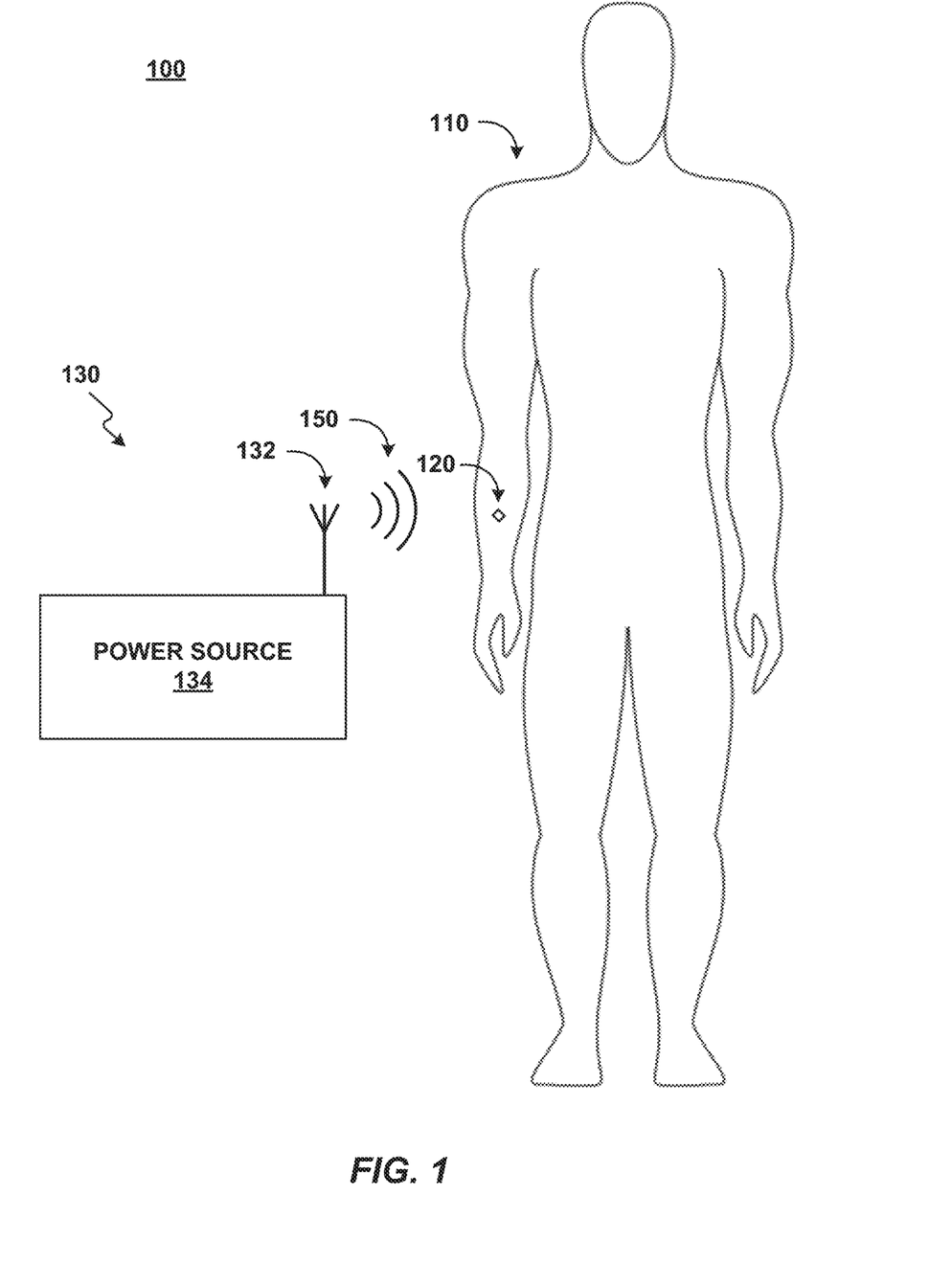
FIG. 1 is a diagram of an example system environment for implementing embodiments consistent the present disclosure.

FIG. 1 depicts an example system environment 100 for implementing embodiments of the present disclosure. As shown in FIG. 1, system environment 100 includes a number of components. It will be appreciated from this disclosure that the number and arrangement of these components is exemplary only and provided for purposes of illustration. Other arrangements and numbers of components may be utilized without departing from the teachings and embodiments of the present disclosure.

As shown in the example embodiment of FIG. 1, system environment 100 includes an implanted device 120 and a power system 130. In some embodiments, implanted device 120 is positioned in a subject 110. Subject 110 may be a human subject, an animal subject, or any other type of living subject. In some embodiments, implanted device 120 may be a centimeter implanted device (i.e., a device having size dimensions at least one centimeter each), a millimeter implanted device (i.e., a device having size dimensions less than one centimeter but at least one millimeter each), or a sub-millimeter implanted device (i.e., a device having size dimensions less than one millimeter each). As illustrated in FIG. 1, implanted device 120 includes an antenna system and a rectifier for receiving power wirelessly from power system 130 and converting the received power to DC for use by subsystems of implanted device 120. Implanted device 120 may be capable of being implanted at various locations and at various depths within the body of subject 110. While implanted device 120 is shown in FIG. 1 to be implanted in the arm of subject 110, other implant locations are contemplated and the illustrated example is in no way intended to be limiting on the present disclosure.

Implanted device 120 may include one or more subsystems for performing various functions. Examples of an implanted device include a vestibular prosthesis having subsystems for augmenting and/or repairing one or more functions of a subject 110's vestibular system, a micro sensor or telemetry device having subsystems for collecting data about various bodily systems of subject 110, a brain-computer interface device having subsystems for sensing brain activity of subject 110 and converting the sensed signals to instructions for performing various physical actions, a drug delivery device, a neural stimulation device, and a pain stimulation device. Other example implanted devices may be used in conjunction with the disclosed embodiments, however, and the enumerated examples are in no way intended to be limiting on the scope of the present disclosure.

Power system 130 may include one or more ex-vivo antenna systems 132 and one or more power sources 134. Antenna system 132 may be capable of transmitting and receiving signals at various radio frequencies using power from power source 134. For example, power source 134 may generate power and provide it to antenna system 132, and antenna system 132 may wirelessly radiate the generated power. Each power source 134 may be implemented by using any conventional power generation system, such as a portable (e.g., battery operated) or fixed (e.g., a lab power supply) power source, a variable or constant power source, etc. In some embodiments, each antenna system 132 is paired with a single power source 134. In other embodiments, a power source 134 may be provide power to one or more antenna systems 132, or each antenna system 132 may receive power from one or more power sources 134.

Each antenna system 132 may include one or more antenna elements (referred to herein as loops). The design aspects of antenna system 132 (e.g., loop location, spacing, size and power, signal frequency, etc.) may be optimized for different implanted devices 120, different applications (e.g., different subjects 110), different implant locations, etc. For example, some antenna systems 132 may be designed to be held close to the skin of subject 110 (e.g., on the skin of subject 110 or a few millimeters away from the skin). Other antenna systems 132 may be designed to be held further away. Accordingly, these differences in location may drive antenna size, loop spacing, signal frequency, etc.

Transmitted signals 150 may include instructions such as, for example, instructions for implanted device 120 to perform telemetry by capturing data about the environment in which it is implanted. Transmitted signals 150 may alternatively, or in addition, include sufficient power for supplying implanted device 120 with power to run any subsystems included in implanted device 120. Received signals may include data such as, for example, sensed or measured data, still images, video, audio, etc.

Antenna system 132 may transmit and receive data and power using various near-field or intermediate-field transmission techniques. Such techniques may include non-radiative transmission techniques such as near/intermediate-field coupling. Examples of near/intermediate-field coupling include inductive coupling and capacitive coupling. In some embodiments, where power system 130 and implanted device 120 communicate via inductive coupling, antenna system 132 may generate a magnetic near-field to transmit data and/or power to implanted device 120. In some embodiments, where power system 130 and implanted device 120 communicate via capacitive coupling, antenna system 132 may generate an electric near-field to transmit data and/or power to implanted device 120.

Figure 2:
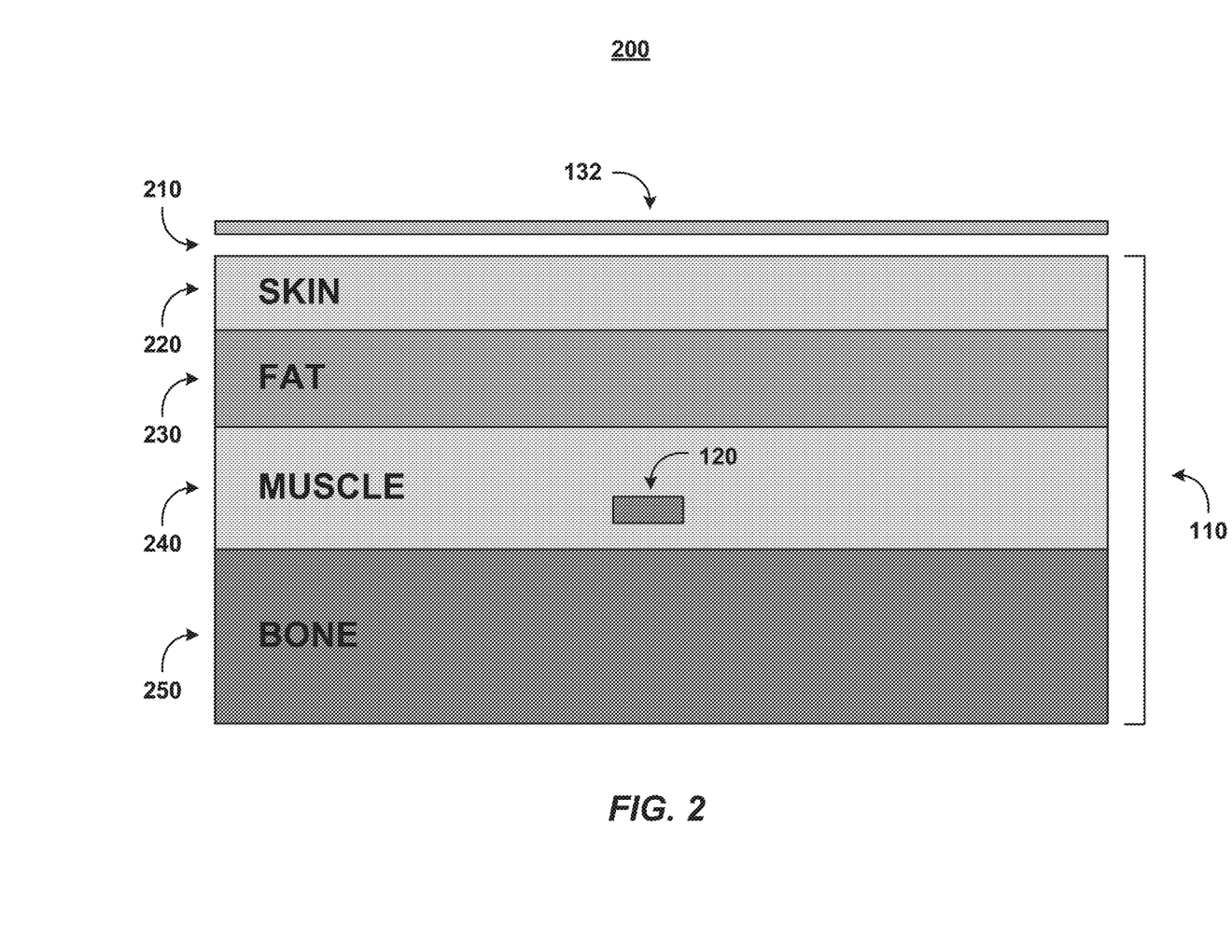
FIG. 2 is a cross-sectional view of a portion of the example system environment shown in FIG. 1.

FIG. 2 illustrates a cross-sectional view 200 of the example system environment 100 shown in FIG. 1. As shown in cross-sectional view 200, implanted device 120 may be implanted in muscle layer 240 of subject 110. Antenna system 132 may transmit power wirelessly to implanted device 120 through skin layer 220, fat layer 230, and muscle layer 240 of subject 110. Each layer 220-240 of subject 110 may provide varying levels of attenuation to the transmissions of antenna system 132. Antenna system 132 may be held close to skin layer 220 of subject 110, leaving an air gap 210 of various distances (e.g., 5-10 mm). While antenna system 132 may be held directly against skin layer 220, leaving an air gap 210 between antenna system 132 and skin layer 220 may act as an insulator that helps to minimize tuning defects and stabilizes the transmission frequency of antenna system 132. While an air gap 210 is used to isolate antenna system 132 from skin layer 220 in the example shown in FIG. 2, other electrical insulators may be used. Examples of electrical isolators include, glass, ceramic, paper, A.B.S., acrylic, fiberglass, and nylon. In some embodiments, antenna system 132 may be packed in an insulating material to achieve similar results from providing air gap 210.

Figure 3:
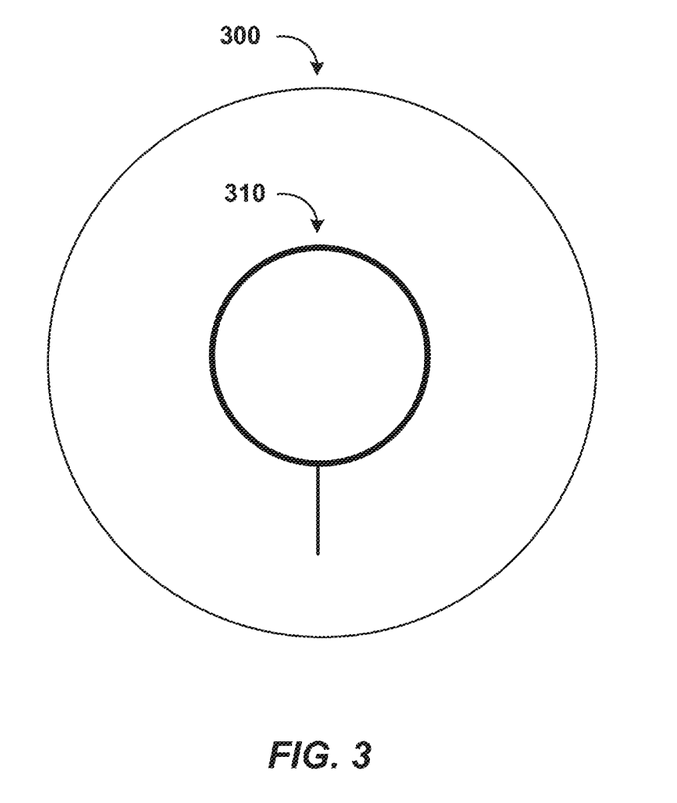
FIG. 3 is an illustration of an example antenna system for providing wireless power with a single loop design that lacks beam focusing characteristics.

FIG. 3 illustrates an example antenna system 300 with a single antenna loop 310 for providing power to an implanted device. Loop 310 may be circular in shape and may be physically coupled to the surface of one side of antenna system 300. A power source may provide power to antenna system 300. Antenna system 300 may provide the power wirelessly to one or more implanted devices by radiating the power through loop 310.

Figure 4A:
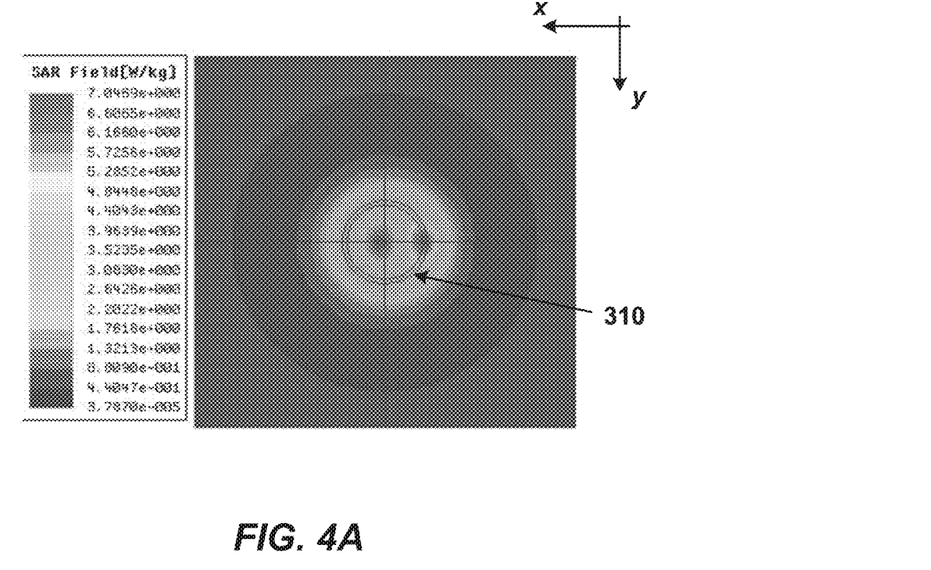
FIGS. 4A and 4B illustrate various performance characteristics of the example antenna system illustrated in FIG. 3.
Figure 4B:
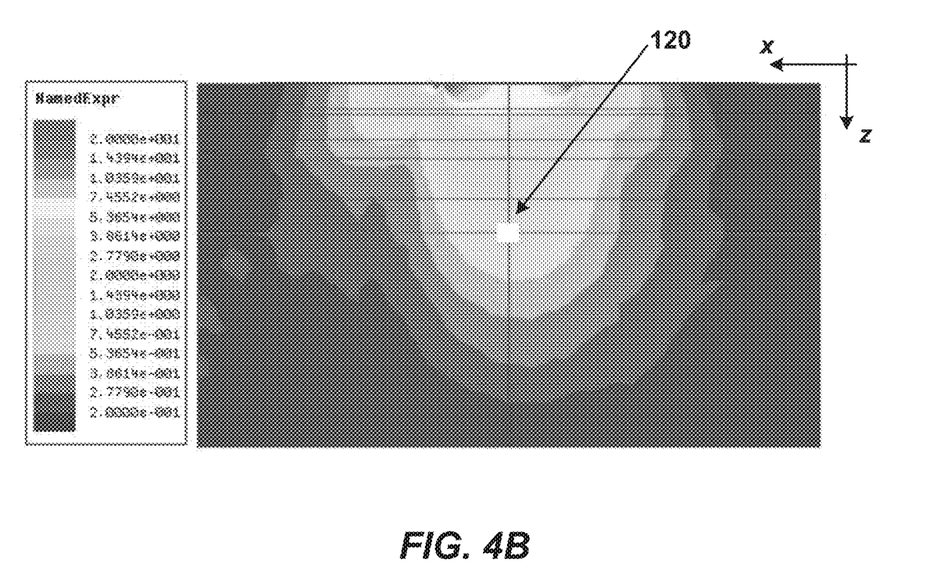

FIGS. 4A and 4B are graphical representations of various performance characteristics associated with single loop, antenna system 300 of FIG. 3. FIG. 4A is a heat map showing a top-down view of the specific absorption rate and distribution of the RF electromagnetic energy radiated by antenna system 300. The intensity of the head map represents the specific absorption rate, which is the rate at which the RF electromagnetic energy is absorbed into the human body. As shown in FIG. 4A, the power distribution of antenna system 300 is mostly uniform around loop 310 with the exception of a hotspot at the left side of loop 310. Power intensity drops off quickly, however, as it radiates inwardly and away from loop 310, resulting in poor distribution uniformity in the x-y plane.

FIG. 4B is a heat map showing a cross-sectional view of the SAR and distribution of electromagnetic energy radiated by single loop, antenna system 300. As shown in FIG. 4B, the specific absorption rate of antenna system 300 drops of quickly as the transmitted electromagnetic energy radiates into the body toward implanted device 120. One of the primary causes of the poor signal penetration of antenna system 300 is a lack of beam focusing capabilities. A significant amount of power is radiated away from the implanted device, thereby resulting in poor power transfer efficiency and increased specific absorption rate.

Figure 5A:
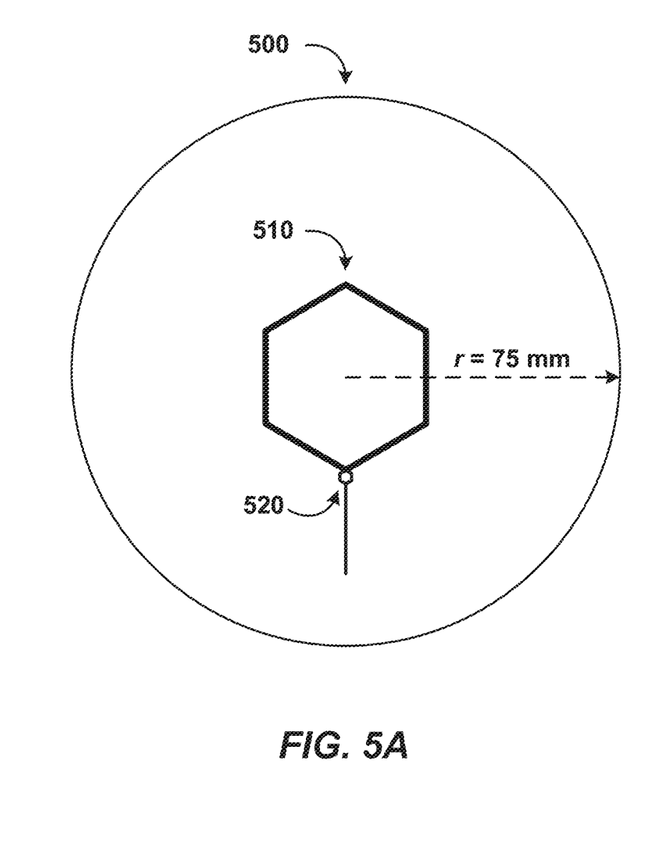
FIGS. 5A and 5B illustrate an example embodiment of an antenna system for providing wireless power, in accordance with embodiments of the present disclosure.
Figure 5B:
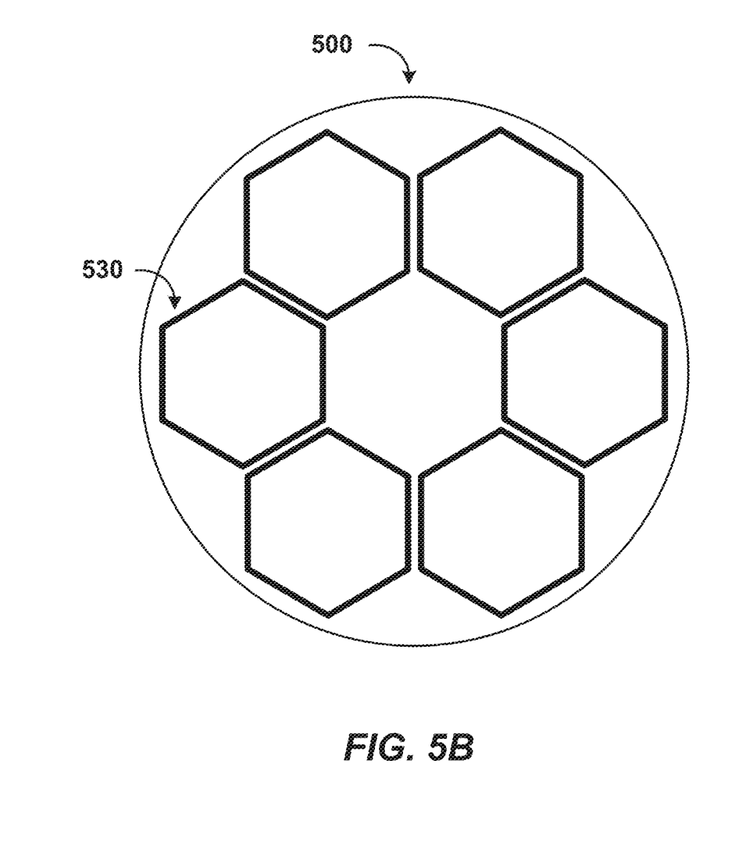

FIGS. 5A and 5B illustrate an example antenna system 500, in accordance with embodiments of the present disclosure. Antenna system 500 may be used to implement one or more aspects of antenna system 132 of FIG. 1, while addressing one or more of the shortcomings of antenna system 300 described above. As shown in FIGS. 5A and 5B, antenna system 500 includes a primary antenna loop 510, a matching network 520, and one or more parasitic antenna loops 530. It will be appreciated from this disclosure that the number and arrangement of these components is exemplary only and provided for purposes of illustration. Other arrangements and numbers of components may be utilized without departing from the teachings and embodiments of the present disclosure. By way of example, in some embodiments antenna system 500 may be implemented as a disc-shaped structure having a radius of approximately 75 mm, as shown in FIG. 5A. Other dimensions and structures may be implemented, consistent with the teachings of this disclosure.

FIG. 5A illustrates a primary side of antenna system 500. Primary loop 510 and matching network 520 may be physically coupled to the surface of the primary side. A power source (e.g., power source 134 of FIG. 1) may provide power to primary loop 510 through matching network 520. Matching network 520 may be implemented as a network of electrical circuit components (e.g., capacitors, resistors, inductors, etc.) and may be used to match the impedance of antenna system 500 to the input impedance of the power source at the desired operating frequency. Accordingly, the configuration of components included in matching network 520 may depend on various design characteristics, such as transmit frequency of antenna system 500, the size and placement of primary loop 510 and parasitic loops 530, etc.

FIG. 5B illustrates a secondary side of antenna system 500. In some embodiments, the secondary side may be a side of antenna system 500 opposing the primary side. In some embodiments, the secondary side may be a layer stacked on top of the primary side. As shown in FIG. 5B, one or more parasitic antenna loops 530 may be physically coupled to the surface of the secondary side. Parasitic loops 530 may be positioned so as to absorb some of the power radiated by primary loop 510 that would otherwise be radiated away from implanted device 120 and absorbed by the body of subject 110. Parasitic loops 530 may reradiate the absorbed power, thereby focusing the total power radiated by antenna system 400 toward implanted device 120. Accordingly, the positioning of parasitic loops 530 forms a constructive interference pattern that improves directivity of the power radiated by antenna system 500.

One or a combination of various design characteristics of antenna system 500 may be adjusted in order to maximize the focusing or directivity of antenna system 500 for different applications. One design characteristic that may be adjusted is the size of primary loop 510 and parasitic loops 530. For example, while primary loop 510 and parasitic loops 530 are shown in FIGS. 5A and 5B to all be the same size, primary loop 510 and one or more parasitic loops 530 may be different sizes and/or one or more parasitic loops 530 may be different in size. The number of primary elements 510 and/or parasitic loops 530 included in antenna system 500 may also be adjusted (e.g., increased or decreased). Another design characteristic that may be adjusted is the spacing between primary loop 510 and parasitic loops 530 and/or the spacing between parasitic loops 530. For example, while there is no overlap between primary loop 510 and parasitic loops 530 in FIGS. 5A and 5B, one or more parasitic loops 530 may overlap each other, one or more parasitic loops 530 and primary loop 510 may overlap each other, or any combination thereof. A further design characteristic that may be adjusted is the shapes of primary loop 510 and parasitic loops 530. For example, primary loop 510 and parasitic loops 530 may be hexagonal, square, circular, or any other symmetrical, asymmetrical, or amorphous shapes, or a combination thereof. The orientation of primary loop 510 and/or parasitic loops 530 may also be adjusted. For example, while primary loop 510 and parasitic loops 530 are shown in FIGS. 5A and 5B to be parallel with each other on the x-y plane, any of primary loop 510 and parasitic loops 530 may be rotated about one or more three-dimensional axes.

Variations to the design characteristics of antenna system 500 change the inductive and the capacitive coupling properties between parasitic loops 530 and between primary loop 510 and parasitic loops 530, which, in turn, change the characteristics of constructive interference pattern of antenna system 500. Accordingly, the design characteristics of antenna system 500 may be adjusted to accommodate different shapes and sizes of implanted devices 120, different implant depths (and differing levels of attenuation by extension), different locations at which antenna system 500 is intended to be held (e.g., on the skin, close to the skin, etc.), as well as to ensure that the power system (e.g., power system 130 of FIG. 1) for antenna systems 500 complies with all applicable government and health/safety laws and regulations.

Antenna system 500 may be implemented through various configurations and electromechanical structures. For example, antenna system 500 may include a substrate such as a ridged printed circuit board or a flexible substrate formed to the body shape of a subject 110 wearing antenna system 500. The size and shape of the substrate may be selected according to one or more design parameters (e.g., the size and depth of the implanted device to be powered, the amount of power required by the implanted device, etc.). Primary loop 510, matching network 520, and parasitic loops 530 may be printed thereon. Elements 510-530 may be printed using one or more types of ridged and/or flexible conductive materials such as, for example, copper, gold, silver, aluminum, etc. While primary loop 510 and matching network 520 may be printed on the opposite side of the substrate as parasitic loops 530, other configurations are contemplated without departing from the scope of this disclosure. For example, elements 510-530 may be all printed on the same side of the substrate or one or more parasitic loops 530 may be printed on opposing sides of the substrate.

In addition, additional layers of antenna loops may be added to antenna system 500. For example, an antenna system having a substrate with multiple stacked layers deposited thereon may have a first layer deposited on the substrate that includes a primary loop 510, a second layer including one or more parasitic loops 530 deposited on top of the primary loop 510 layer, and one or more layers of additional parasitic loops 530 deposited on top of the first layer of parasitic loops 530. Each layer of parasitic loops 530 may have design characteristics (e.g., loading capacitance, size, shape, spacing, and number of parasitic loops 530, etc.) similar to, or different from, one or more of the other layers of parasitic loops 530.

Figure 6A:
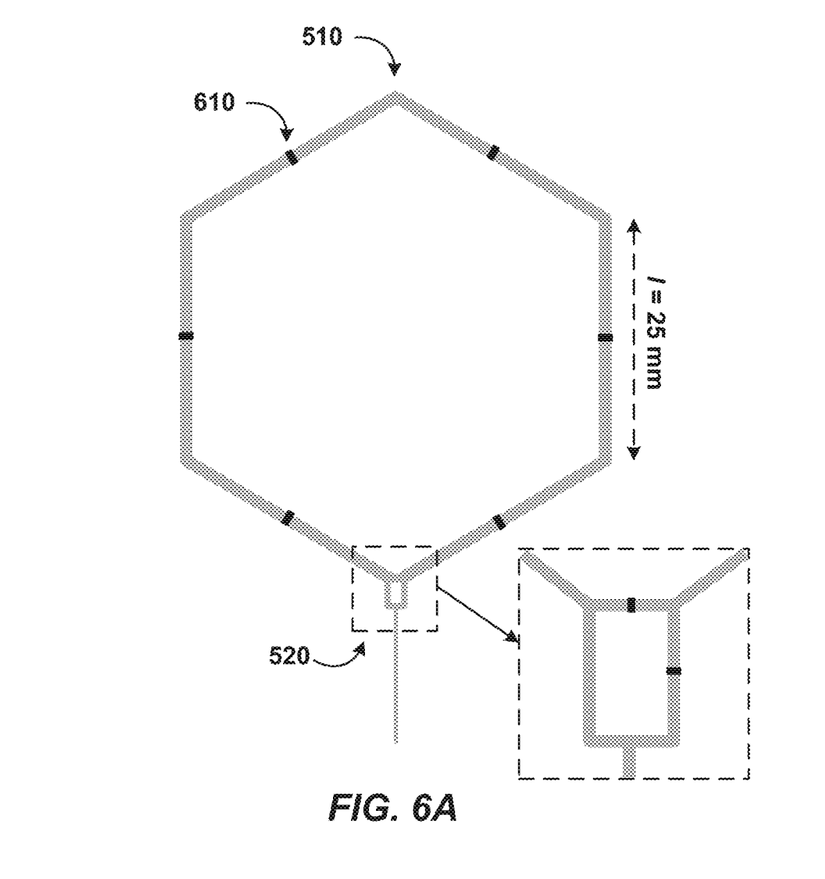
FIGS. 6A and 6B illustrate detailed views of example antenna loops, in accordance with embodiments of the present disclosure.
Figure 6B:
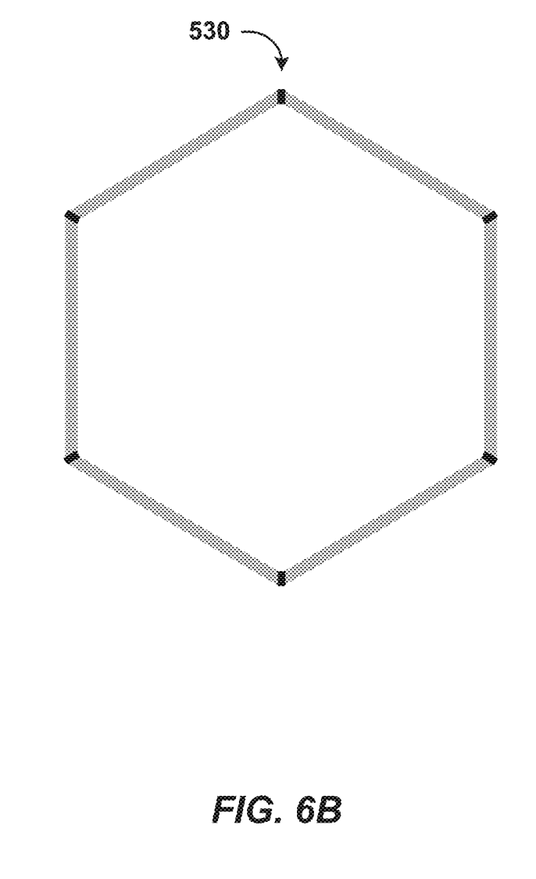

FIGS. 6A and 6B respectively illustrate detailed views of primary antenna loop 510 and a parasitic antenna loop 530 of antenna array 500 shown in FIGS. 5A and 5B. As shown in the example embodiments of FIGS. 6A and 6B, primary antenna loop 510 and parasitic antenna loop 530 may be implemented as hexagonally-shaped structures. By way of example, each segment of the hexagonal structure may have a length of approximately 25 mm, as shown in FIG. 6B. As will be appreciated, other dimensions and structure shapes may be implemented, consistent with the teachings of this disclosure.

In some embodiments, primary loop 510, matching network 520, and parasitic loop 530 may include one or more loading components 610. Loading components 610 may include capacitors, inductors, resistors, and/or other electronic circuit components. The characteristics (e.g., capacitance, inductance, etc.) and placement of loading components 610 may determine the loading capacitance of primary loop 510 and parasitic loops 530. By way of example, in FIGS. 6A and 6B, primary loop 510 may have a loading capacitance of approximately 8.0 pF and each parasitic loop 530 may have a loading capacitance of approximately 7.5 pF. In some embodiments, the characteristics and placement of loading components 610 may be selected to ensure that a uniform magnetic field distribution is generated within the region of primary loop 510 and each parasitic loop 530 when loading components 610 are periodically loaded. The characteristics and placement of loading components 610 on primary loop 510 may be the same as, or different from, the characteristics and placement of loading components 610 on parasitic loops 530. For example, the characteristics and placement of loading components 610 may be selected such that primary loop 510 has a different overall loading capacitance than parasitic loops 530. Similarly, the characteristics and placement of loading components 610 may be the same or different between one or more parasitic loops 530.

Figure 7A:
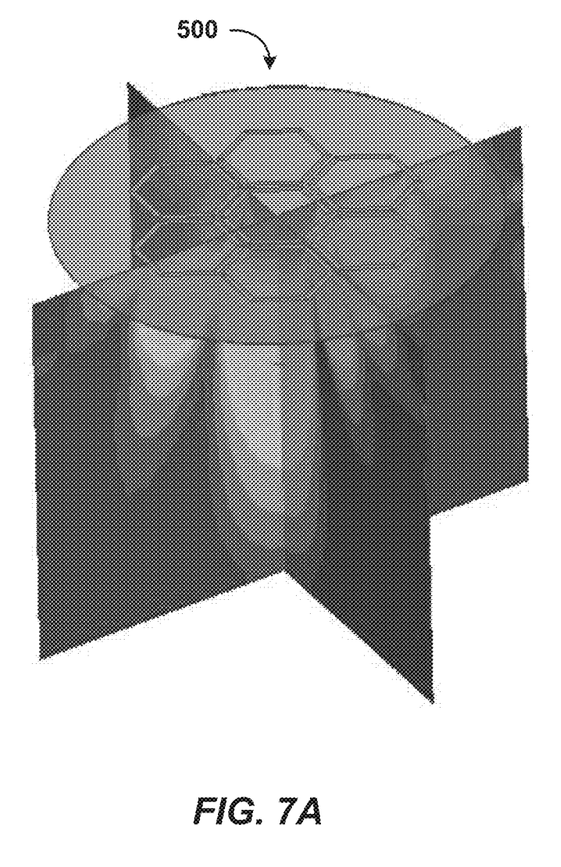
FIGS. 7A-7C illustrate various performance characteristics associated with the example antenna system shown in FIGS. 5A and 5B.
Figure 7B:
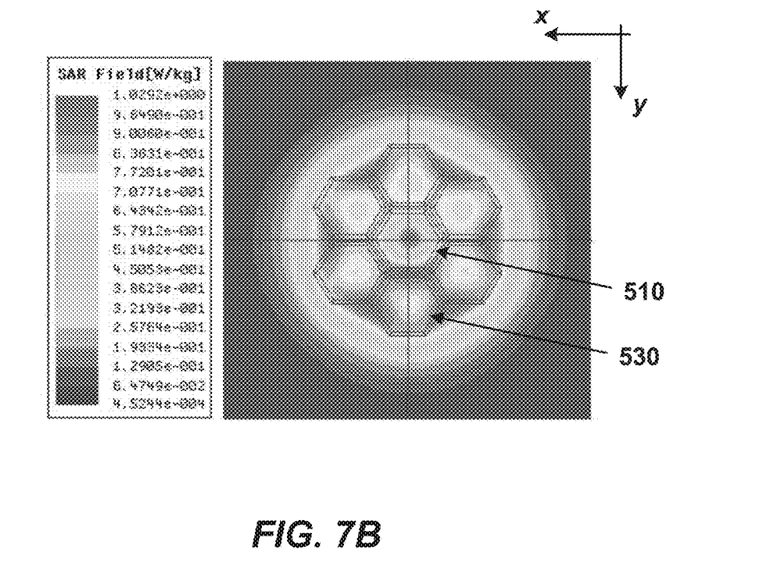
Figure 7C:
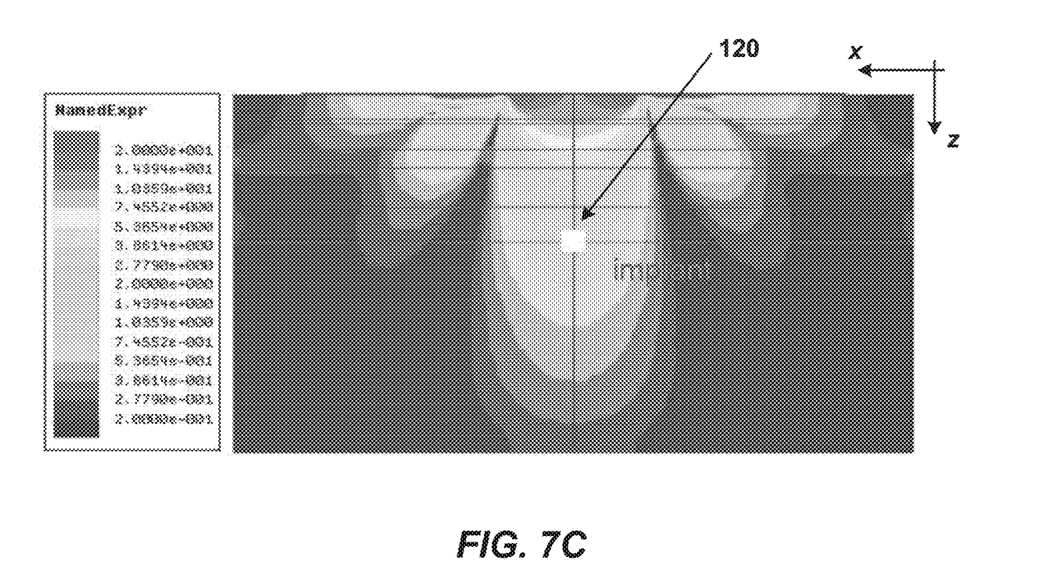

FIGS. 7A-7C are graphical representations of various performance characteristics associated with antenna system 500 of FIGS. 5A and 5B. FIG. 7A is a heat map showing a three-dimensional view of the specific absorption rate and distribution of the RF electromagnetic energy radiated by antenna system 500. FIG. 7B is a heat map showing a top-down view of the specific absorption rate and distribution of the RF electromagnetic energy radiated by antenna system 500. FIG. 7C is a heat map showing a cross-sectional view of the specific absorption rate and distribution of the RF electromagnetic energy radiated by antenna system 500.

As shown in FIGS. 7A-7C, the power radiated by antenna system 500 is distributed broadly and uniformly around primary loop 510 and parasitic loops 530 at the surface of the skin of subject 110. Therefore, for a given power transmission level, the power absorbed by human tissue per area or per volume (as a measurement of SAR) is significantly less for antenna system 500's power transmission compared to antenna system 300. Moreover, the power radiated by antenna system 500 becomes more focused as it travels further into the body due to the constructive interference pattern generated by parasitic loops 530 unlike antenna system 300. Accordingly, the improved directivity provided by the focusing features of antenna array 500 results in greater power transfer efficiency to implanted device 120 compared to the power transfer efficiency of antenna system 300 while minimizing power loss into the body of subject 110.

In the preceding specification, various exemplary embodiments and features have been described with reference to the accompanying drawings. It will, however, be evident that various modifications and changes may be made thereto, and additional embodiments and features may be implemented, without departing from the broader scope of the invention as set forth in the claims that follow. For example, advantageous results still could be if components in the disclosed systems were combined in a different manner and/or replaced or supplemented by other components. Other implementations are also within the scope of the following exemplary claims. The specification and drawings are accordingly to be regarded in an illustrative rather than restrictive sense. Moreover, it is intended that the disclosed embodiments and examples be considered as exemplary only, with a true scope of the present disclosure being indicated by the following claims and their equivalents.

What is claimed is:

1. An antenna system for providing wireless power to an implanted device in a body of an individual, comprising:
   a primary antenna loop for receiving power from a power source and radiating the power received from the power source toward the implanted device, the primary antenna loop defining a first perimeter; and
   one or more parasitic antenna loops for absorbing a portion of power radiated by the primary antenna loop and reradiating the absorbed portion of the power radiated by the primary antenna loop toward the implanted device, at least one of the one or more parasitic antenna loops positioned entirely outside the first perimeter of the primary antenna loop, each of the at least one of the one or more parasitic antenna loops defining a respective second perimeter, and wherein the primary antenna loop is positioned outside each of the respective second perimeters,
   wherein the power radiated by the primary antenna loop and the reradiated power by the at least one of the one or more parasitic antenna loops form a wireless power transmission pattern that is distributed at a surface of an individual's skin to reduce a specific absorption rate of such power at the surface of the individual's skin and becomes more focused as it travels into the body of the individual toward the implanted device.

2. The antenna system according to claim 1, wherein the primary antenna loop and the at least one parasitic antenna loop are printed on a substrate.

3. The antenna system according to claim 2, the primary antenna loop and the at least one parasitic antenna loop are printed on a same surface of the substrate.

4. The antenna system according to claim 2, wherein:
   the primary antenna loop is printed on a first surface; and
   the at least one parasitic antenna loop is printed on a second surface of the substrate, the first and second surfaces being different surfaces.

5. The antenna system according to claim 4, wherein the first and second surfaces are on opposing sides of the substrate.

6. The antenna system according to claim 4, wherein the second surface is stacked on top of at least a portion of the first surface.

7. The antenna system according to claim 2, wherein the at least one parasitic antenna loop includes a plurality of parasitic antenna loops.

8. The antenna system according to claim 7, wherein a portion of at least two of the parasitic antenna loops overlap on the substrate.

9. The antenna system according to claim 7, wherein at least two of the parasitic antenna loops are the same shape.

10. The antenna system according to claim 1, wherein the primary antenna loop and the at least one parasitic antenna loop include loading capacitors periodically loaded to form a uniform magnetic field distribution.

11. The antenna system according to claim 10, wherein loading capacitance of the primary antenna loop is different from loading capacitance of the at least one parasitic antenna loop.

12. The antenna system according to claim 1, wherein the primary antenna loop and the at least one parasitic antenna loop are different shapes.

13. The antenna system according to claim 1, further comprising:
   a matching network connecting the primary antenna loop to the power source, the matching network for matching impedance of the antenna system with impedance of the power source.

14. The antenna system of claim 1, wherein at least one of the one or more parasitic antenna loops is positioned entirely outside the perimeter of the primary antenna loop, and wherein each of the at least one of the one or more parasitic antenna loops defines a respective second perimeter, and wherein the primary antenna loop is positioned outside each of the respective second perimeters.

15. An antenna system for providing wireless power to an implanted device in a body of an individual, comprising:
   a primary antenna loop for receiving power from a power source and radiating the power received from the power source toward the implanted device in the body of the individual, the primary antenna loop defining a first perimeter; and
   a plurality of parasitic antenna loops for forming a constructive interference pattern that focuses radiated power received from the primary antenna loop as it travels toward the implanted device in the body of the individual and reduces a specific absorption rate of such power at a surface of the individual's skin, at least one parasitic antenna loop of the plurality of parasitic antenna loops positioned entirely outside the first perimeter of the primary antenna loop, each of the at least one of the one or more parasitic antenna loops defining a respective second perimeter, and wherein the primary antenna loop is positioned outside each of the respective second perimeters.

16. The antenna system according to claim 15, wherein loading capacitance of the primary antenna loop is different from loading capacitance of the parasitic antenna loops of the plurality of parasitic antenna loops.

17. The antenna system according to claim 15, wherein the primary antenna loop and at least two of the parasitic antenna loops of the plurality of parasitic antenna loops are printed on a flexible substrate.

18. The antenna system according to claim 15, further comprising:
   a matching network connecting the primary antenna loop to the power source, the matching network for matching impedance of the antenna system with impedance of the power source.

19. The antenna system according to claim 15, wherein the primary antenna loop and at least two of the parasitic antenna loops of the plurality of parasitic antenna loops are printed on a substrate using at least one of gold, copper, and silver.

20. The antenna system according to claim 15, wherein a size of the primary antenna loop is different from a size of the plurality of parasitic antenna loops.

21. A handheld device for providing wireless power to a device implanted in a body of an individual, comprising:
   a housing graspable and usable while held by a user;
   a power source disposed within the housing;

an antenna system disposed within or on the housing, the antenna system comprising:
- a primary antenna loop for receiving power from a power source and radiating the power from the power source toward the device implanted in the body of the individual, the primary antenna loop printed on a first surface of a substrate and defining a first perimeter;
- a matching network for connecting the primary antenna loop to the power source, the matching network printed on the first surface of the substrate; and
- a plurality of parasitic antenna loops for reducing a specific absorption rate of radiated power received from the primary antenna at a surface of the individual's skin and for improving a transfer efficiency of the radiated power from the primary antenna loop by focusing the radiated power received from the primary antenna as it travels toward the device implanted in the body of the individual, each parasitic antenna loop of the plurality of parasitic antenna loops printed on a second surface of the substrate and positioned outside the first perimeter of the primary antenna loop.

\* \* \* \* \*